US008779333B2

(12) United States Patent
Collins et al.

(10) Patent No.: US 8,779,333 B2
(45) Date of Patent: Jul. 15, 2014

(54) COLUMN HEATER

(75) Inventors: David Collins, Celbridge (IE);
Ekaterina Nesterenko, Dublin (IE);
Brendan Heery, Kells (IE); Brett Paull, Hobart (AU)

(73) Assignee: Dublin City University, Dublin (IE)

( * ) Notice: Subject to any disclaimer, the term of this patent is extended or adjusted under 35 U.S.C. 154(b) by 433 days.

(21) Appl. No.: 13/134,831

(22) Filed: Jun. 17, 2011

(65) Prior Publication Data

US 2012/0318782 A1  Dec. 20, 2012

(51) Int. Cl.
*F27D 11/00* (2006.01)
*F25B 29/00* (2006.01)

(52) U.S. Cl.
USPC ............. 219/438; 165/58; 204/451; 392/411; 73/23.4

(58) Field of Classification Search
USPC ........... 219/441, 438; 204/451, 602; 392/411, 392/422, 417; 73/23.41, 23.39, 23.42, 73/61.57, 61.52–61.53, 61.55
See application file for complete search history.

(56) References Cited

U.S. PATENT DOCUMENTS

2004/0173457 A1* 9/2004 Miller et al. .................. 204/451

* cited by examiner

*Primary Examiner* — Shawntina Fuqua
(74) *Attorney, Agent, or Firm* — Seed IP Law Group PLLC

(57) ABSTRACT

A direct contact segmented column heater is described. The heater is capable of a broad heating and cooling range, and exhibits a very rapid response, with heating and cooling rates better than 350° C. min$^{-1}$. In one configuration one or more of the individual heating devices are provided with full independent control and temperature feedback, and developed to provide excellent thermal stability at all temperatures. The heating devices or in other words active thermal transfer devices are capable of bi-directional operation, selectively heating (i.e., providing heat to) or cooling (i.e., withdrawing heat from) a column and/or contents of a column.

35 Claims, 12 Drawing Sheets
(8 of 12 Drawing Sheet(s) Filed in Color)

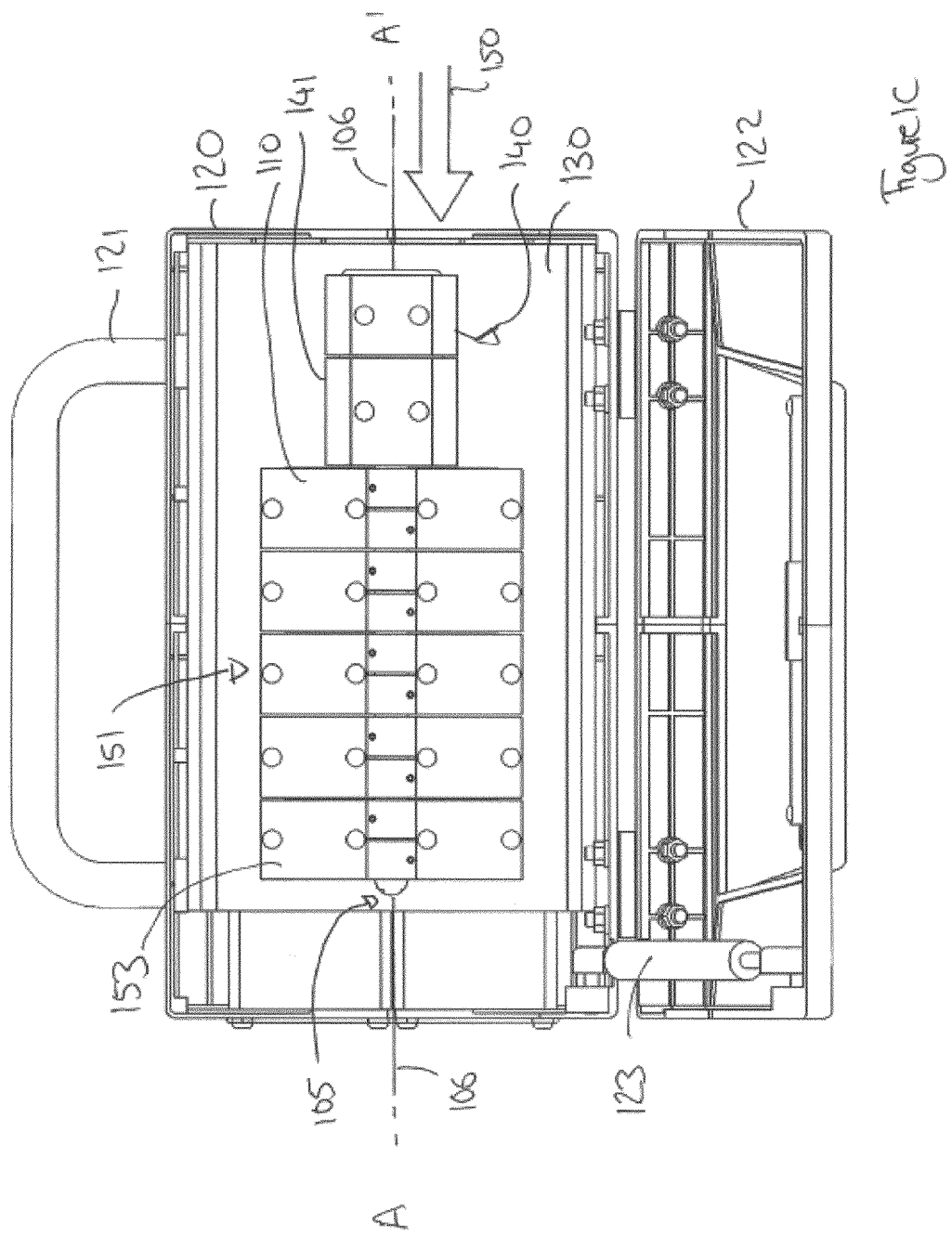

COLUMN HEATER

FIELD

The present application relates to column heaters/coolers and particularly to a column heater that is useable in regulation of column temperature. Such regulation has particular application within the context of the present teaching for both liquid and gas chromatography applications. The application more particularly relates to a column heater that is configured to provide a differential heating along a longitudinal axis of the column.

BACKGROUND

Regulation of column temperature in liquid chromatography (LC) is less common than in gas chromatography (GC), nevertheless temperature is an important, yet often neglected, separation parameter. Precise control of column temperature can, and has been used to manipulate run times, affect peak efficiency and resolution, increase analyte signal to noise ratios, and even reduce mobile phase solvent consumption, the latter being currently of interest in the area of "green chromatography". Numerous studies have reported these advantages when using elevated column temperatures in high-performance liquid chromatography/high-pressure liquid chromatography (HPLC), for various modes of liquid chromatography.

Separations carried out at high temperatures also provide the opportunity to apply higher flow rates without the usual increased pressure penalty, due to the decreased viscosity of the mobile phase. The combination of the above mentioned decrease in retention (particularly in reversed-phase mode) and the ability to apply higher than usual flow rates, mean that high temperature separations can achieve tremendous reductions in analysis times, compared to separations carried out at room temperature, up to 50 times faster in some instances. This is particularly relevant in the move towards fast LC and GC, so fast separations are important. Current ovens cannot provide the heating rates required for use with fast separations and so are completely useless when it comes to fast LC.

Typically the known full temperature operating region of high temperature HPLC could perhaps be defined as extending from 60° C. to 374° C., since many of the commonly used solvents in reversed-phase separations would otherwise boil at approximately 65° C., and 374° C. is the highest critical temperature observed for water. Of course there are many techniques that go beyond these limits, such as those that rely on the use of super-critically heated water as the mobile phase, or those at the at the other end of the temperature scale, including some approaches which utilize column cooling below 0° C. In all cases, performing HPLC at non-ambient temperatures requires an accurate, precise and well regulated control of temperature during the separation process, this being particularly important where temperature gradients are being applied. However, it is clear that the task of precise temperature control throughout the column in HPLC is far from trivial, and achieving such temperature precision with rapid gradients generates more difficulty. For example, in addition to "programmed" or intentional applied thermal profiles, there may also be unintentional heating within the column from frictional forces or other causes of non-uniform temperature profiles, which may even cause band broadening and loss of efficiency.

With most modern HPLC systems, various difficulties in obtaining precise and responsive control of column temperature can arise. These are primarily dependent upon type of column oven, but also upon the column dimensions, stationary phase parameters, eluent flow rate and fluid pre-heaters etc. In many instances, the column heater set-point may differ from the actual column temperature by several degrees and temperature variation can occur internally along the length of the column oven, if mobile phase temperature is significantly different to that of the column. In addition, flow rates generating large pressure drops along the column have been suggested to generate frictional heating, especially at pressures above 600 bar, where such heating can be dramatic. In some cases, longitudinal temperature gradients within the column may increase to the point that the column outlet temperature can be over 10° C. higher than the column inlet.

To overcome the problem of temperature differentials at the column inlet, it is known that when elevated temperatures are utilised for the separation, the temperature of the incoming mobile phase should be within ±6° C. of the oven/column temperature, to minimize any band broadening resulting from radial temperature gradients.

It is known to control the temperature of the column in various ways: heating blocks, water jackets and baths, as well as the common circulating air ovens. Conventionally, heaters based upon water jackets and baths have been found to be the most efficient, due to their superior heat capacity. However, such column heaters generally exhibit a rather limited temperature range (though water can be replaced with other liquids with greater heat capacity, for temperatures greater than 100° C.), and a prohibitively slow rate of heating and cooling, in applications where any form of temperature gradient is required. In the case of heating blocks, performance strongly depends on the degree of contact with the column, and in commercial examples where this close contact is maintained, these type of heaters are generally efficient in heat transfer, and also exhibit reasonable heating rates, of approximately 20-30° C. min$^{-1}$. Circulating air ovens have a heating capacity that depends on the heating rate of the air and speed at which this heated air can be circulated around the column. In general, circulating air based ovens are mainly suitable for isothermal operation. As with liquid bath ovens, and most heating block ovens, circulating air ovens are very limited in their heating and cooling rates, typically <10° C. min$^{-1}$. In each of the above cases, it can be argued that current performance levels are unsuitable for many fast HPLC applications, particularly those which may require rapid thermal equilibration, such as cases where the application of rapid temperature gradients over short periods is required.

Very few commercially available column ovens are capable of heating beyond 80° C., while fewer still are capable of cooling below 10° C. Gas chromatographic ovens have been used to achieve temperatures as high as 350° C., for ultra-high temperature HPLC; however this approach also has obvious practical limitations, again including relatively slow heating/cooling rates.

There is therefore a need for a column heating arrangements that could address these and other problems. There is also a need for a column cooling arrangement that could address these and other problems.

SUMMARY

These and other problems are addressed by a column heater comprising a plurality of individual active thermal transfer devices, referred to herein as heating devices) which are configured to be arranged in an array along a longitudinal axis of the column. By providing individual heating devices it is possible to specifically target individual regions of the column with a specific heating regime. Furthermore the use of individual heating devices in accordance with the present teaching allows for generation of very fast thermal gradients without using undue amounts of energy. In a first arrangement, the individual heating devices are provided in a modular construct that allows the length of the array to be varied dependent on the length of the column that requires heating. The column heater may also be arranged to provide a targeted cooling regime and within the present context the term "heating device" is intended to define a device that is capable of generating or providing both a heating and/or cooling function to the column. The term heating device is used interchangeably herein with the term active thermal transfer devices to refer to an active device capable of bi-directional operation, selectively heating (i.e., providing heat to) or cooling (i.e., withdrawing heat from) a column and/or contents of a column.

A column heater in accordance with the present teaching is particularly useful in capillary and micro-scale HPLC applications and may be considered a chromatographic column heater. In chromatographic applications, such dimensions of column lend very well to rapid heating and high temperature operation, as the column mass is small and the columns have thin walls (predominantly manufactured in fused silica housing), thus possessing low thermal mass and high thermal conductivity. As a result, the columns can achieve rapid thermal equilibration. By allowing generation of longitudinal thermal gradients along the length of the column the present teaching advantageously addresses problems associated with the known art.

In a first configuration the heating devices are based upon Peltier thermoelectric (TEC) units. In accordance with the present teaching it is possible to use such active devices to combine the advantages of direct contact ovens (fast thermal transfer rates) and of circulating air ovens (broad elevated temperature range). Heating devices provided in accordance with the present teaching enable rapid direct contact active thermal transfer (i.e., active heating and/or active cooling) through the use of an array of TEC units, which would consist of many distinct thermally isolated zones, making it possible to generate both temporal and spatial temperature gradients. This precise and rapid localized control of temperature using individual devices arranged in a linear array provides, in accordance with the present teaching, high performance chromatographic applications.

The advantages of such a design include the usual advantages of applied temperature, such as increased separation efficiency, variation of peak selectivity, and decreased run times, but also allowing to spatially apply heated or cooled zones for on-column thermally controlled trap-and-release applications and other thermally responsive polymers or to apply instant or dynamic temperature gradients to the column, the latter of which provides insights into frictional heating related band broadening processes within capillary columns. Finally, such a heating/cooling platform is useful as a tool in various hyphenated techniques that demand minimal extra column band broadening and require either high and low temperatures, which are outside the normal operating envelope of most column heaters.

A direct contact segmented heater provided in accordance with the present teaching is capable of a broad heating and cooling range, and exhibits a very rapid response, with heating and cooling rates which are on the order of 400° C. min$^{-1}$. In one configuration one or more of the individual heating devices are provided with full independent t control and temperature feedback, and developed to provide excellent thermal stability at all temperatures.

These and other advantages will be appreciated from the following description which will assist in an understanding of the present teaching but is not intended to limit the teaching in any way.

BRIEF DESCRIPTION OF THE DRAWINGS

The patent or application file contains at least one drawing executed in color. Copies of this patent or patent application publication with color drawings will be provided by the Office upon request and payment of the necessary fee.

The present application will now be described with reference to the accompanying drawings in which:

FIG. 1C shows the heater of FIG. 1A in plan view;

DETAILED DESCRIPTION

The following description is provided to assist the person of skill in understanding the present teaching but is not intended to limit the scope to the exemplary arrangements which are described.

Figure 1A:
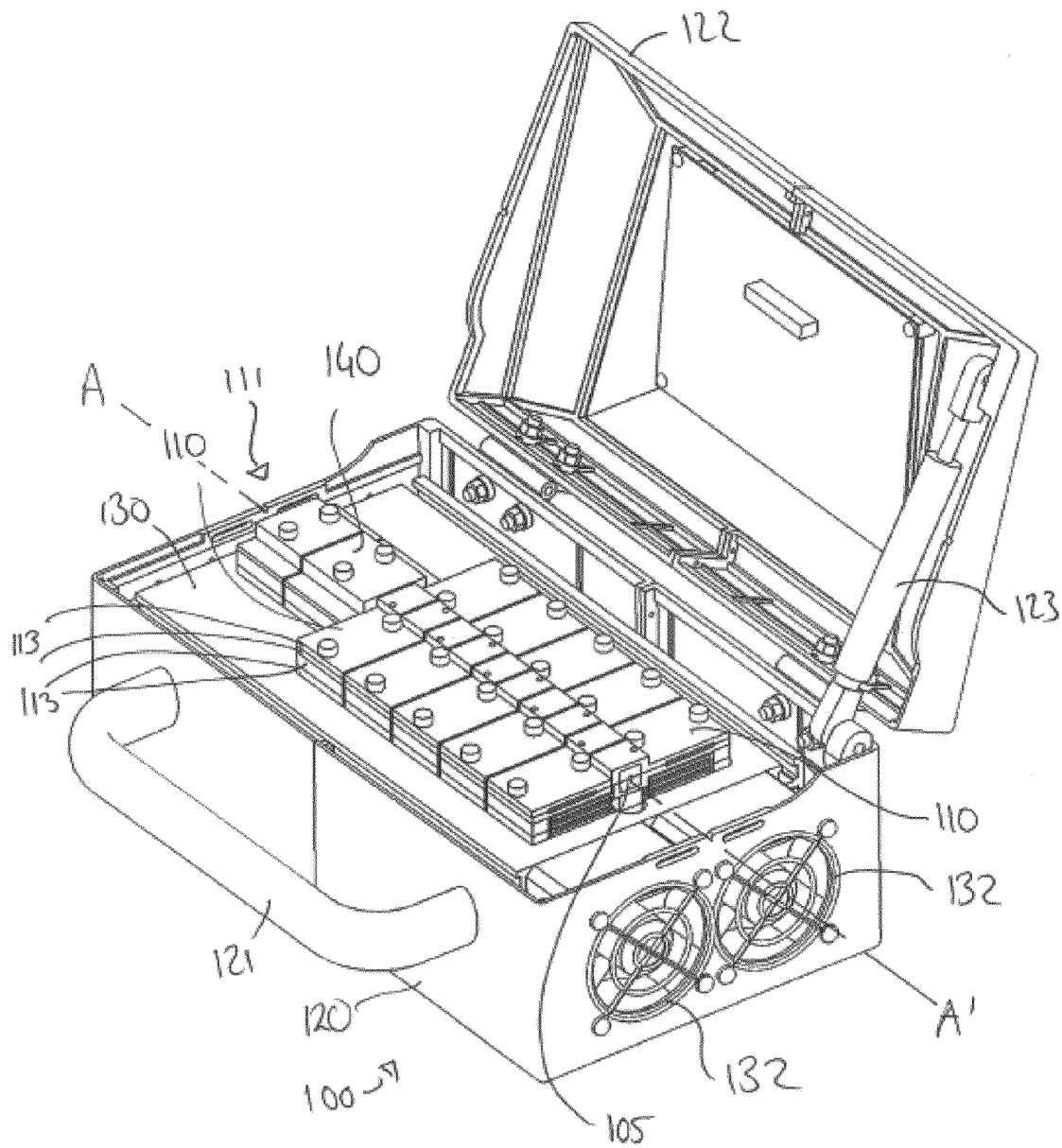
FIG. 1A shows in schematic perspective form an exemplary column heater provided in accordance with the present teaching with a capillary column attached.
Figure 1B:
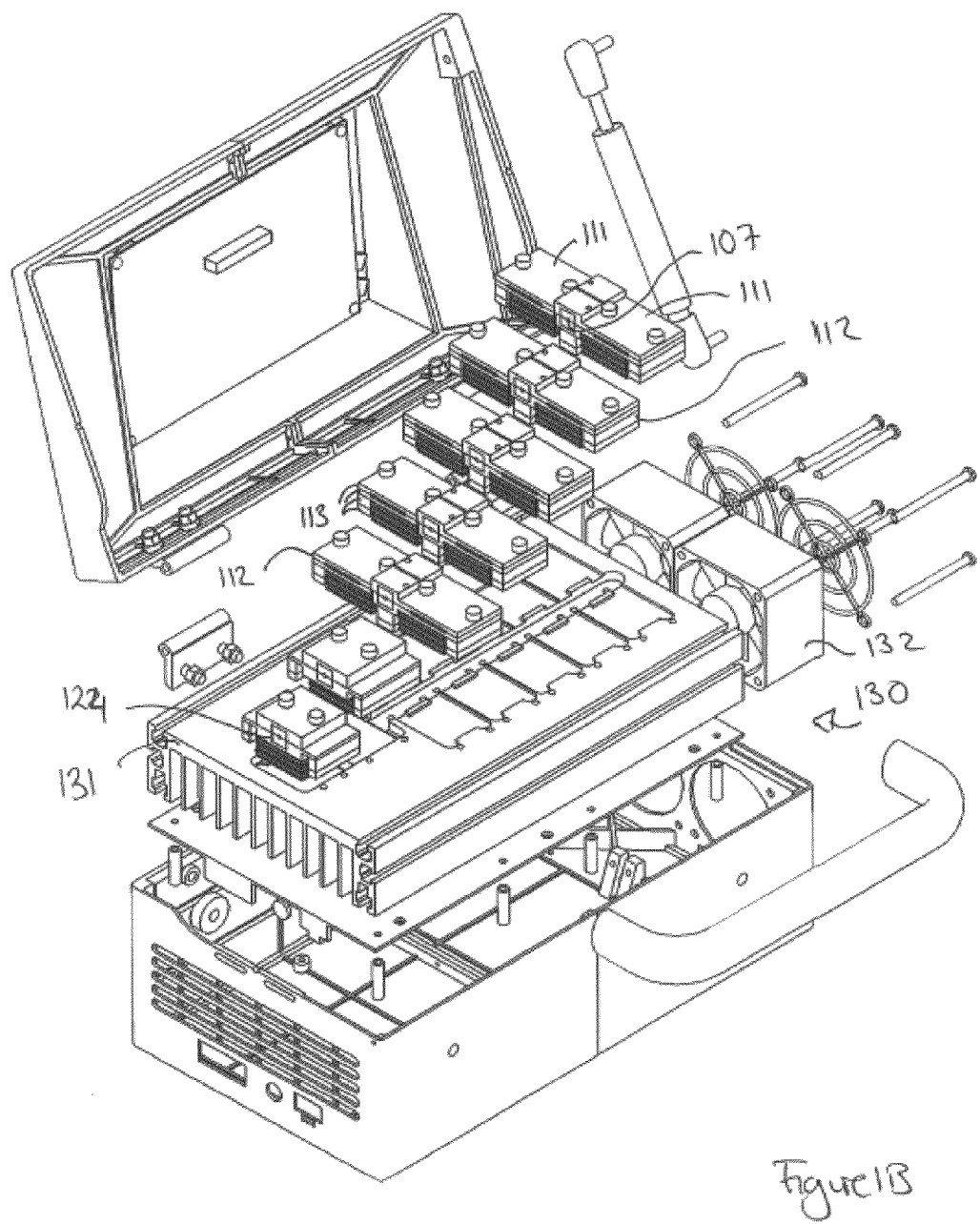
FIG. 1B shows the heater of FIG. 1A in an exploded view.

As shown in FIGS. 1A to 1C an exemplary column heater 100 provided in accordance with the present teaching comprises a channel 105 for receipt of a column 106—shown in the plan view of FIG. 1C. The channel is desirably dimensioned to accommodate a capillary or microscale column. Such columns are known in the art and are conventionally fabricated from a silica based material. The heater of the present teaching is particularly useful when used in conjunction with capillary or micro-bore columns which will further facilitate the control of the column temperature, due to the low heat capacity of such columns and therefore negligible radial temperature gradients.

A plurality of individual heating devices 110 are provided. The individual heating devices are configured to be arranged in an array 111 along, and proximal to, a longitudinal axis A-A' of the channel 105.

In use, and as shown in FIG. 1C, a column 106 is presented to the channel such that the column and the heaters extend along the longitudinal axis A-A' of the column 120.

In the exemplary arrangement of FIG. 1, the heater 100 is located within a box 120 which includes a handle 121 and a lid 122. The lid, in this exemplary configuration, is pivotably connected via a telescopic rod 123 to the main volume of the box so as to allow the heater to be fully retained within a closed box. By use of the handle, a user may transport the heater 100, the dimensions being such as to be highly portable.

As the dimensions of the box constrain the length of the channel it is not easy in this exemplary configuration to extend the length of the channel. However in other configurations, the modular nature of the individual heating devices and the ease in which they can be coupled together can be readily used to vary the length of a heating zone provided by the column heater of the present teaching. In this way a user can add heating devices as appropriate for their application. The modularity of the individual heating devices is clear from FIG. 1B where each heating device is provided as a block or stand-alone unit 112 having heating surfaces 111 provided on either side of a channel portion 107. By mounting a plurality of blocks relative to one another it is possible to define the extended channel and plurality of individual heating zones. In a fully assembled array each of the channel portions 107 will be co-linear with one another such that the column will be retained in a straight line within the heating zones defined by the plurality of individual units.

By providing individual heating devices it is possible to specifically target individual regions of the column with a specific heating regime. In this exemplary configuration the individual heating devices 110 are provided as individual Peltier thermoelectric (TEC) devices or units. In the arrangement of FIG. 1, individual units 110 are located on both sides of the channel 105 but other configurations could provide the heating devices to one side of the channel only.

Peltier TEC units are known typically provide cooling by acting as a very effective heat pump, drawing heat from one side of the device and emitting it on the other and their mode of operation will be known to the person of skill in the art and will not be detailed here. It will be appreciated that the level of cooling that can be achieved by TEC units depends on the amount of heat that can be drawn away from the hot side of the device and the ability of the attached heat-sink to dissipate the heat. The direction of heat transfer through the device depends on its polarity, so by simply switching the polarity of the TEC unit in the circuit, it is possible to both heat and cool each individual unit. This facility of the Peltier TEC units is advantageously employed within the context of the present teaching to provide targeted heating or cooling of specific regions of the column as required.

While the TEC's 110 may be provided as single unit, the present inventors have realised that the use of TECs in piles (sandwiched together) gives better performance and allows use over a broader temperature range. FIGS. 1A and 1B show an exemplary arrangement of four individual TEC's 113 stacked one upon the other in a layering arrangement to form the final pile. It will be appreciated that in this exemplary arrangement identical TECs are used in the pile. In other configurations progressively smaller or larger ones could be stacked one upon the other. It will be appreciated however that by using identical TEC's the flow heat in either direction is provided with the same efficiency which is desirable where the intended application will make use of both the cooling and heating effect that is possible using these types of devices. In another configuration one or more of the individual TEC piles may be coupled with a resistive heating element. An example of such a resistive element is a Kapton® heater provided by TEMPCO Electric Heater Corporation which will be considered exemplary of a resistive heating element. By using an active flexible surface heater of which a Kapton® heater is an exemplary form it will be appreciated that the resistive heater element(s) could be interlaced with the individual layers of the TEC piles—such as between the individual layers 113 shown in FIG. 1B to provide a boost in rapid ramping when required.

Whereas TEC piles exist commercially, they are typically sized to flow heat in only one direction. The TEC piles provided in accordance with the present teaching are specifically configured to allow a flow of heat in both directions, to obtain both heating and cooling of a target. Typical ranges achievable using a heater in accordance with the present teaching is a temperature range from the sub zero environment (<−10° C.) to 200° C. or more.

In the example of FIG. 1 the array comprises five TEC piles arranged co-linearly. The channel 105 is proximal to the array. By locating the column within the channel, it is possible to provide a direct heating of the region of the channel proximal to the individual heating device. It will be appreciated that the heating/cooling effect is provided in this configuration in a direction transverse to the longitudinal axis of the channel.

Using the heating devices creates a heat source within the heater that desirably needs to be dissipated. In the configuration of FIG. 1 a simple forced air cooled heat exchanger 130 is used. This exemplary arrangement comprises a heat sink 131 on which air from two fans 132 may be directed. During operation below ambient temperature, air is passed from the heat exchanger through a series of fins attached to the bottom surface of each TEC unit (the side which would be heating up), and so by dissipating this heat it allows the working surface of the unit to cool.

By suitably configuring each of the individual units 110 it is possible to provide different levels of heating along the array. This independent control of the heating zones is particularly advantageous. In certain application it is possible to provide both heating and cooling simultaneously and independently along the array. This independent control could be facilitated through the use of individual switches but it will be appreciated that such control is advantageously implemented in one or more other hardware or software configurations without departing from the scope of the present teaching. In an exemplary configuration the control is automated using control logic provided on a processing device.

In the arrangement of FIG. 1, the column is provided in the form of a capillary column and on receipt within the channel is thermally coupled to the array of TEC units using thermally conductive flexible silicon or gel 124 which allows the use of columns of varying sizes up to 3 mm in outside diameter. The gel 124 is located into the channel and provides a seat for the column. In this way the channel defines a region or volume for receipt of a gel, the gel then providing a seat for the received column. Depending on the dimensions of the column, the elastomeric nature of the gel may be sufficient to allow it to deform about and retain the column within the gel. In another configuration where the diameter of the columns being used is greater, it may be necessary to provide a cut-out in a surface of the gel of suitable dimension to receive the column. The gel may in certain configurations be provided as a removable block which can be removed from the channel. By providing blocks of differing configurations the column heater may be easily used with different columns—simply by judicious selection of an appropriate block of gel for seating the column within the channel.

Such a gel 124 may be formed from flexible silicon or the like and desirably has thermal conductivity properties sufficient to allow the heating/cooling effect of the individual devices to have a corresponding effect on the located column. The flexible nature of the gel is particularly advantageous as it provides good thermal conductivity over a large area, ensuring that the heating/cooling effect provided by the units is transferred to the column located within the channel. Furthermore the flexible nature of the gel accommodates a plurality of different capillary dimensions ensuring that the same column heater may be used sequentially with different column types. In another configuration a commercially available thermal paste could be used. What is important is that the column is seated relative to the heating units 110 in a fashion that, ensures good thermal conductivity between the TEC unit surfaces and the column over all or a large portion of the surfaces thereof. Since the thermal paste or silicon gels are not an adhesive, they also allow for the easy removal of the column. It will be appreciated therefore that while an elastomeric gel is particularly advantageous that alternatives that allow a seating and retention of the column within the channel may be used.

Figure 2:
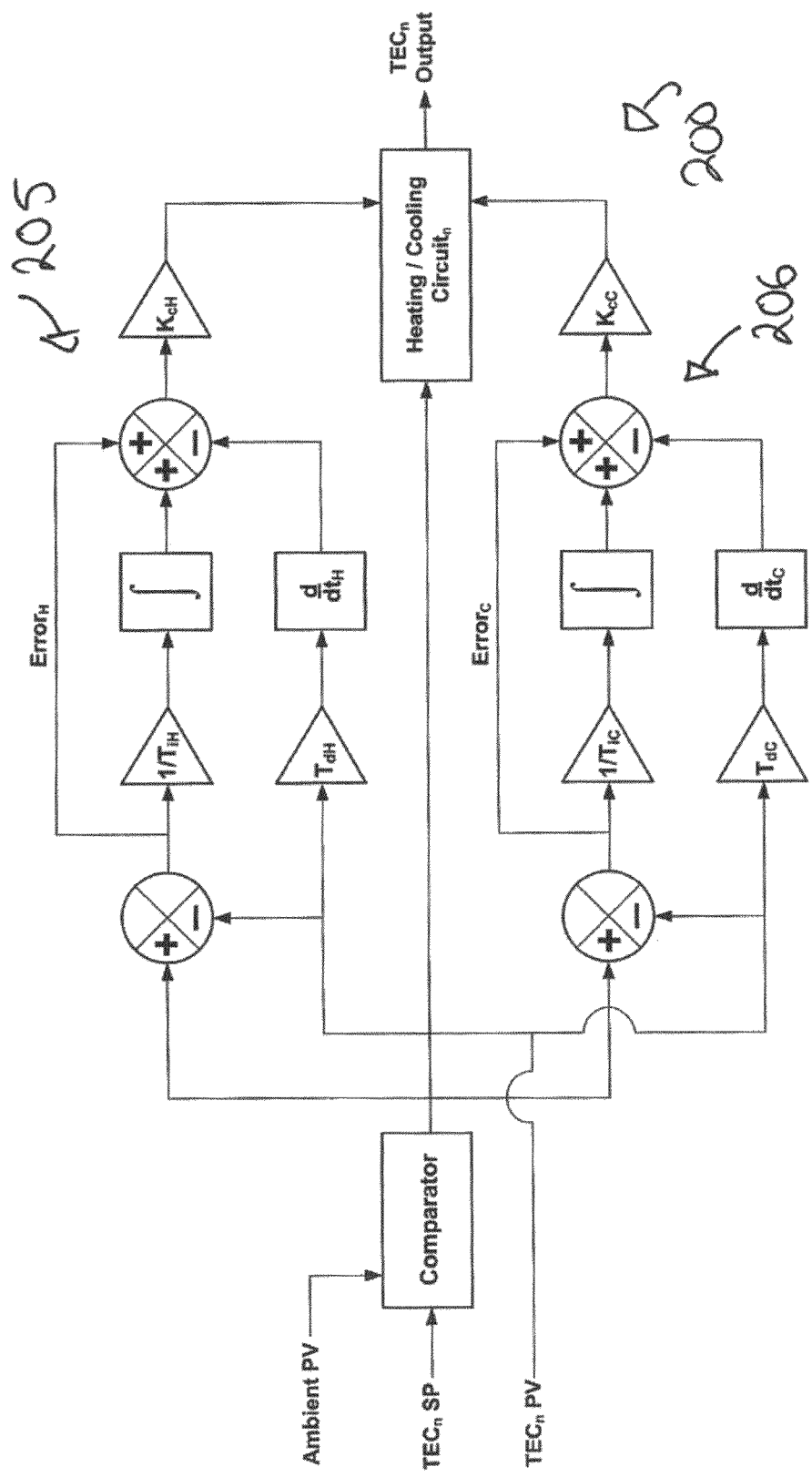
FIG. 2 is an example of a control circuit that may be usefully employed within the context of the present teaching where each heating device has a dedicated PID controller with PV=process variable, SP=set point $1/T_i$, $1/T_d$, $K_c$=control loop response parameters.

To provide accurate temperature control of the heating regime, the heater may comprise a temperature monitor. In the configuration of FIG. 1, the achieved heating of the device was achieved by monitoring the temperature of each individual TEC unit. A thermistor (such as that provided by EPCOS AG, Munich, Germany), which will be appreciated is an example of a heat sensor that may be used to sense temperature, was mounted on the surface of each unit 110, and measures the surface temperature. The data output was fed to a data acquisition circuit which collected data from each segment of the module. Each value was fed into a temperature management program which automatically controlled the temperature of each unit through closed loop control. Closed loop control (in this example through use of a proportional-integral-derivative (PID) control) compares the desired set point with the process value, changing the output to the system (the TEC units) to reach that set point. A schematic of exemplary control circuitry 200 is shown in FIG. 2.

The use of modular heating units per the present teaching also allows for the provision of pre- and/or post heating/cooling of the column. Pre-heating is particularly advantageous for heating an eluent as part of a chromatographic process. Post-cooling is also useful. In the arrangement of Figure where a mobile phase will be introduced into the column heater in the direction indicated by the arrow 150 (see FIG. 1C), two individuals segments 140, 141 are provided upstream of the column heating zone 151 proper. The first unit is a mobile phase pre-heating block and the next one is fitting heating block. The very last unit 153 of the array TECs (or multiple units of the array) as desired) can function as a post-cooling block. The capacity to individually and independently vary the heating or cooling effect provided along different lengths of a column is particularly advantageous. It is also possible to use the individual heating units for effecting a heating of the fittings ensuring that the temperature desired is accurately provided.

To control the applied heating, the column heater desirably comprises a feedback heating loop whereby the sensed heat is then used to drive the applied heat. In the configuration of FIG. 2, each device 110 has two dedicated PID (Proportional-Integral-Derivative) controllers 205,206, one PID loop 205 handling heating operations, while the other 206 controlling cooling. This set up is advantageous in that the thermal response of each TEC unit is different depending on whether the module was in heating or cooling mode. By using this approach the user can very effectively 'tune' the control loops for heating and cooling, and so high ramp rates and fast thermal response are possible while obtaining a high precision with minimal overshoot.

As an example of the application of a heater provided in accordance with the present teaching a number of experiments were conducted. A first experiment pertained to the use of such a heater in chromatographic applications. In such an application it is necessary to first fabricate the column. It will be appreciated that the following specifics are not intended to limit the teaching to that described, and modifications can be made without departing from the spirit and scope of the present teaching.

Chemicals and Reagents

Lauryl methacrylate (LMA), ethylene dimethacrylate (EDMA), butyl methacrylate (BuMA) 1-propanol, 1-4-butanediol, styrene, divinylbenzene (DVB), 3-methoxysilylpropyl methacrylate, 1-decanol and UV-initiator dimethoxy-2-phenyacetophenone (DAP) were all purchased from Sigma-Aldrich (Gillingham, UK). All solvents which were used for the preparation of HPLC mobile phases, and for the synthesis and washing of prepared monoliths, namely, tetrahydrafuran (THF), acetonitrile (ACN), and methanol (MeOH), were purchased from Lab Scan (Gliwice, Poland). The thermal initiator, 1,1'-azobisiziobutyronitrile (AIBN), was obtained from DuPont (Le Grand Sacconex, Switzerland). Standard solutions of ethylbenzene, propylbenzene, butylbenzene and pentylbenzene (purchased from Sigma Aldrich, Gillingham, UK) and toluene (purchased from Lab Scan, Gliwice, Poland), were prepared in 50:50 $ACN/H_2O$ mixture, in a concentration of 0.05 mg/mL for each analyte. Deionised water purified by a Milli-Q system (Millipore, Bedford, USA) was utilised throughout the experiments. Teflon-coated fused silica capillary, 100 μm I.D., 0.375 mm O.D. was purchased from Composite Metal Services Ltd. (Charlestown, UK).

Instrumentation

For the chromatographic studies, an Dionex Ultimate 3000 nano-HPLC system (Dionex, Sunnyvale, Calif., USA) was used, incorporating an FLM3100 column compartment which was used only for the performance comparison with the TEC array module. For data acquisition Chromeleon 6.8 software (Dionex, Sunnyvale, Calif., USA) was utilised. Chromatography was performed with a flow rate of 1 μL $min^{-1}$ and detection was by UV at 254 nm using a 3 nL flow cell. A SputterCoater S150B (BOC Edwards, Sussex, UK) was utilised for coating capillary monolithic stationary phase samples with 60 nm gold layer prior scanning electron microscopy (SEM) analysis, which was performed on a S-3400N instrument (Hitachi, Maidenhead, UK). Optical microscopy evaluation of micro-fluidic chip samples was performed on a Meiji Techno EMZ-8TR stereo microscope (Meiji Techno UK Ltd, Somerset, UK). Thermal imaging was performed using a Thermovision A20 infrared camera (FLIR Systems, West Malling, UK).

Columns

Fused silica capillaries as well as micro-fluidic channels were initially pre-treated through activation of the surface silanol groups of the inner walls by sequential flushing with 1 M NaOH, deionised water, 0.1 M HCl, deionized water, and acetone. The pre-treated capillary was silanised using a 50 wt % solution of trimethoxysilylpropyl methacrylate in toluene at 60° C. for 24 h.

Chromatographic separations were performed on a lauryl methacrylate (LMA)-ethylene dimethacrylate (EDMA) monolithic column. The monomer mixture consisted of 24% wt LMA, 16% wt EDMA, 45.5% wt 1-propanol, 14.5% wt 1-4-butanediol, and 0.4% wt of dimethoxy-2-phenyacetophenone (in respect to monomers). The initiator (DAP) was weighed out into the mixture vessel and the porogen mixture (1-propanol and 1-4-butanediol) was added, followed by the monomers. The mixture was vortexed and deoxygenated under a flow of nitrogen for 10 minutes. A desired length of 100 µm I.D. silanised capillary was filled with the monomer mixture and exposed to 2 Jcm$^{-2}$ of UV radiation. The resultant monolithic column was washed with MeOH to remove residual porogen and unreacted monomers.

The polystyrene-divinylbenzene stationary phase was fabricated by on-chip thermal polymerisation in a micro-fluidic channel. The monomer mixture consisted of 20.3% wt styrene, 20.5% wt DVB, 51.2% wt 1-decanol, 8% wt THF, and 1% AIBN (in respect to monomers). The initiator (AIBN) was weighed out into the mixture vessel and the porogen mixture (1-decanol and THF) was added, followed by the monomers. The mixture was vortexed and deoxygenated under a flow of nitrogen for 10 minutes. A 26 mm long glass/silica chip, with rectangular channel dimensions of 50×100 µm, was filled with the monomer mixture and exposed to a heating program on the column heater 100.

Gradient polymerisation was performed on a butyl methacrylate monomer mixture. The monomer mixture consisted of 24% wt BuMA, 16% wt EDMA, 60% wt 1-decanol, and 1% AIBN. AIBN was first dissolved in the porogen, and then monomers were added to the mixture, which was then vortexed, deoxygenated under the flow of nitrogen for 10 minutes and centrifuged. A length of silanised capillary was filled with the monomer mixture and exposed to a profiled heating program on the TEC array module.

Results and Discussion

System Performance

The working temperature range of the column heater was specifically restricted to 15° C. to 200° C. The performance of the system was initially tested by measuring the individual response of each of the units against time, and by also monitoring their thermal stability over time.

Figure 3:
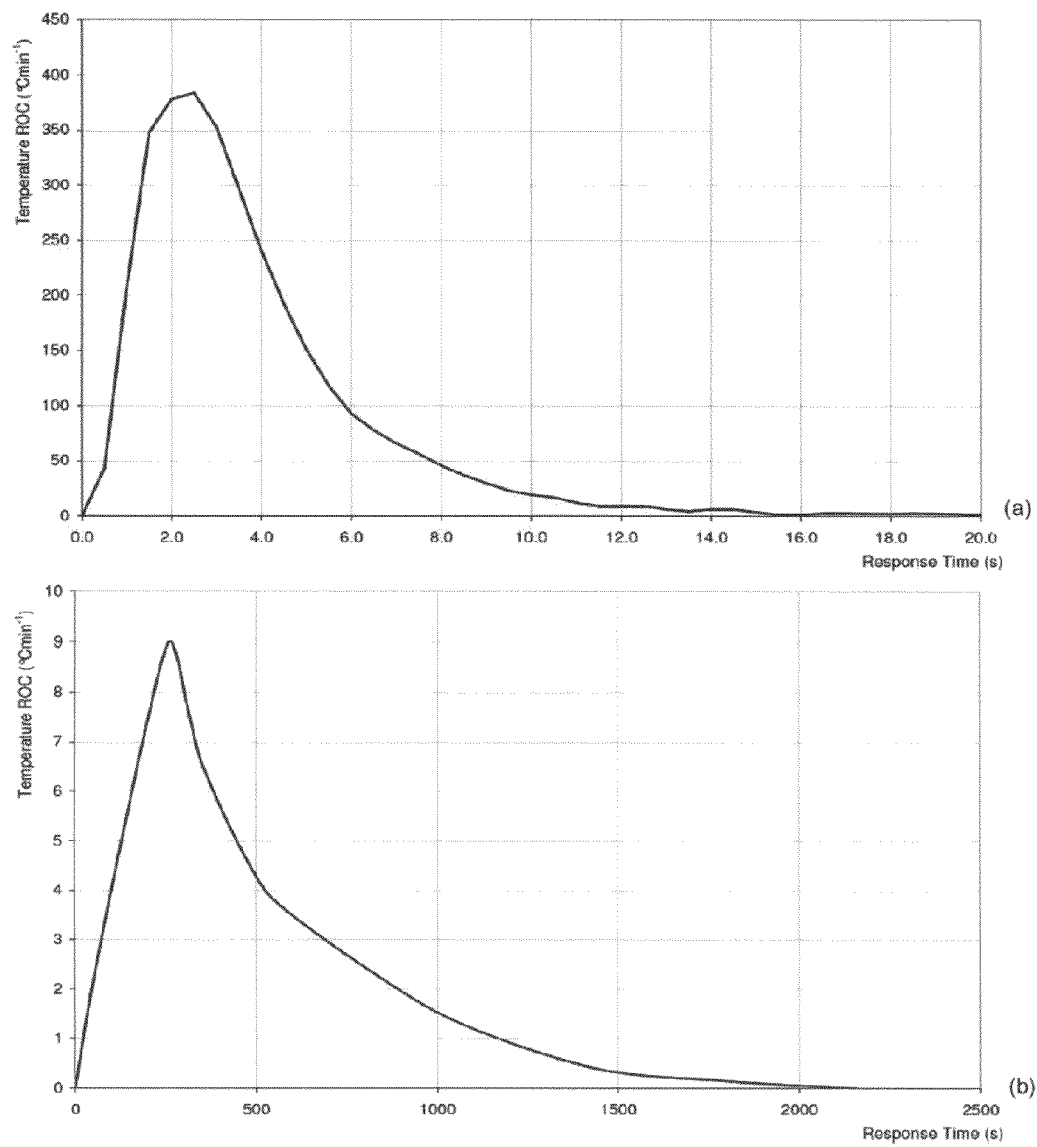
FIG. 3 shows an example of comparison of heating rates between a (a) TEC column oven in accordance with the present teaching and (b) a leading commercially available air bath oven.

It was found that the system response was extremely fast with heating and cooling rates of up to and beyond 360° C. min$^{-1}$. To place this in context, a direct comparison of the module and a leading commercial air bath column oven was made (Dionex Ultimate FLM 3100) with the latter exhibiting a maximum heating rate of just 9° C. min$^{-1}$. Comparing to the commercial column oven, the response of the TEC array heater was approximately 20 times faster. FIG. 3 shows this comparison graphically, comparing the rate of climb (ROC, ° C. min$^{-1}$) against response time (s) for (a) the TEC array module of the column heater of the present teaching and (b) a leading commercially available air bath oven.

Figure 4:
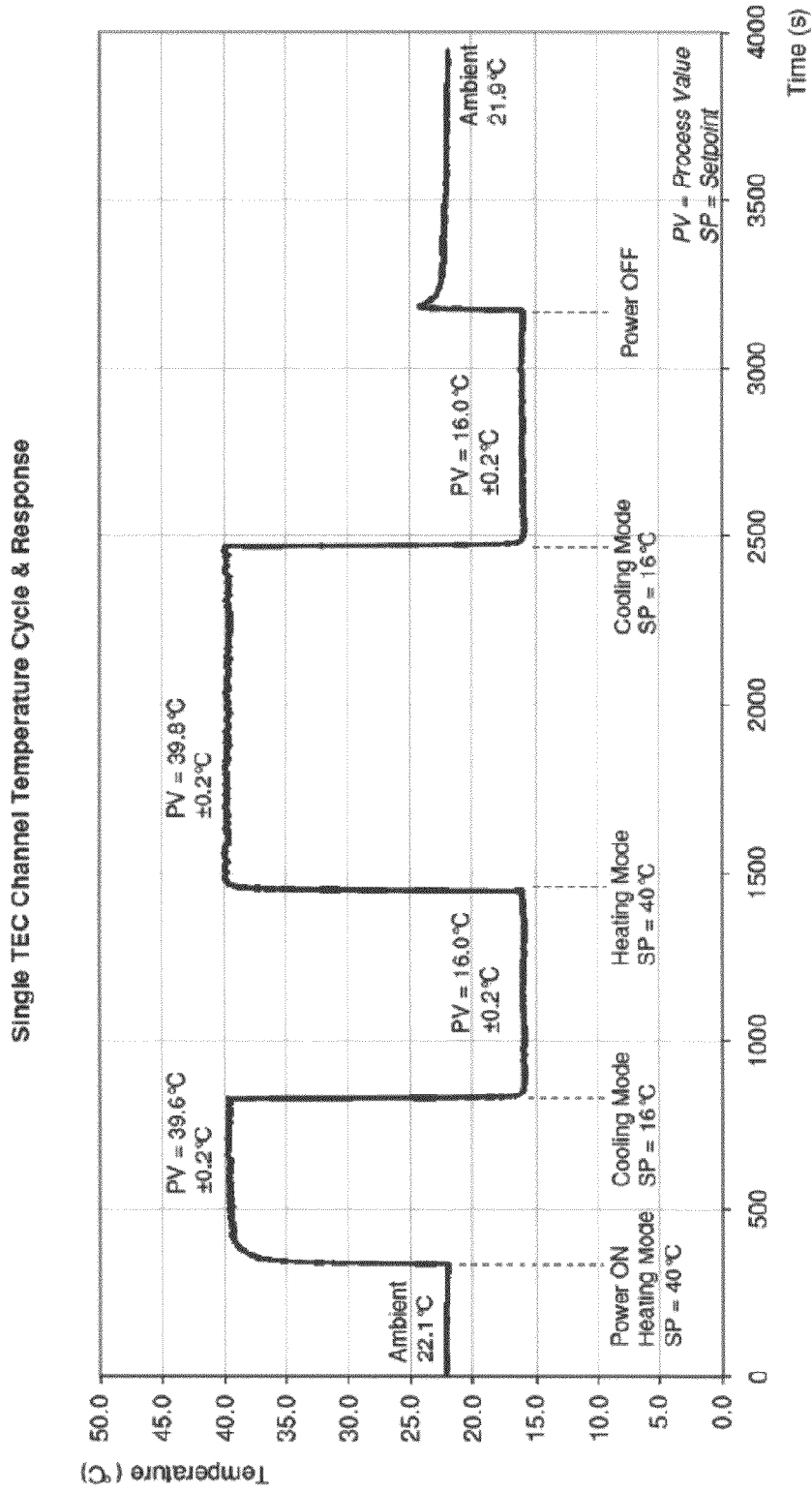
FIG. 4 shows results of an individual heating device response during 1 hr cycling between 16 and 40° C.

The system response and stability were also investigated while continuously cycling between two set point temperatures of 16° C. and 40° C. It was found that the deviation from steady state temperature was in the region of ±0.2° C. over 1 h period and ±0.5° C. over 24 h. FIG. 4 shows a typical cycle and response readout for a single TEC unit over a 1 h period. The inset shows temperature stability at 40° C. over approximately a 15 min period.

The column heating/cooling effectiveness of the TEC array module was evaluated through investigating the rate of column back-pressure change with alteration of temperature. For this study a thermal step gradient program was applied and the column backpressure change was recorded. These results were again compared to those obtained for a commercial air bath oven, for which the same temperature program was used and the backpressure change was studied on the same column (LMA-EDMA polymer monolithic column, 150 mm×100 µm I.D.). For both experiments the flow rate was set to 4 µL min$^{-1}$ (pumping 50% acetonitrile) and the starting temperature was 25° C. The temperature was ramped up to 60° C. in a single step gradient, and once the column temperature reached 60° C., the temperature was set to return directly to 25° C.

Figure 5:
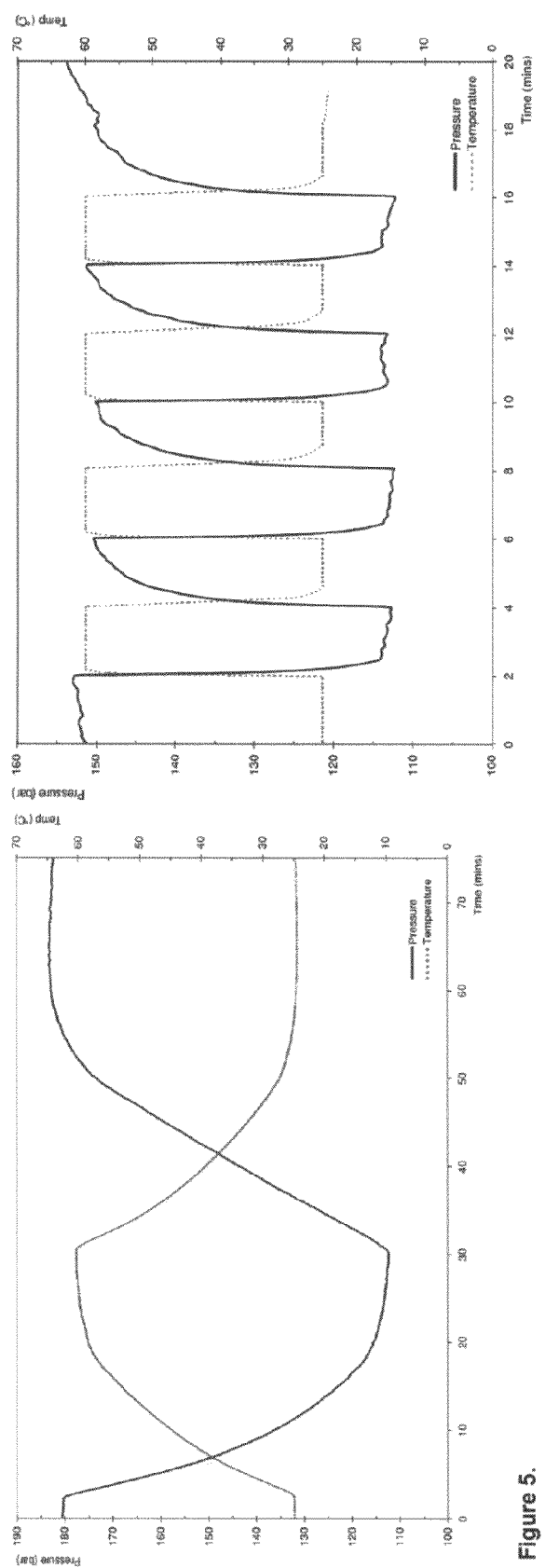
FIG. 5 is a graphical comparison of column temperature and pressure under maximum heating rates for (a) a leading commercially available air bath oven and (b) the TEC column oven

FIG. 5(a) shows the temperature and pressure response of the column for the air bath oven, which had a maximum heating rate of 9° C. min$^{-1}$, taking 28 min to reach set point temperature. This compared with the TEC array module which took less than 30 seconds (see FIG. 5(b)). The completion of the full heating/cooling cycle took approximately 60 min for the air bath oven, compared to less than 4 min for the TEC array module. This demonstration highlights the fact that current commercial air bath type ovens can support only very shallow gradients, outside of which the programmed temperature profile does not match that experienced by the column. Column back pressure profiles, as shown in FIG. 5, are a convenient way of graphically visualizing the rate and degree of actual column temperature change (which is directly related to mobile phase viscosity and therefore column back-pressure), in response to changes in the programmed column temperature.

Figure 6:
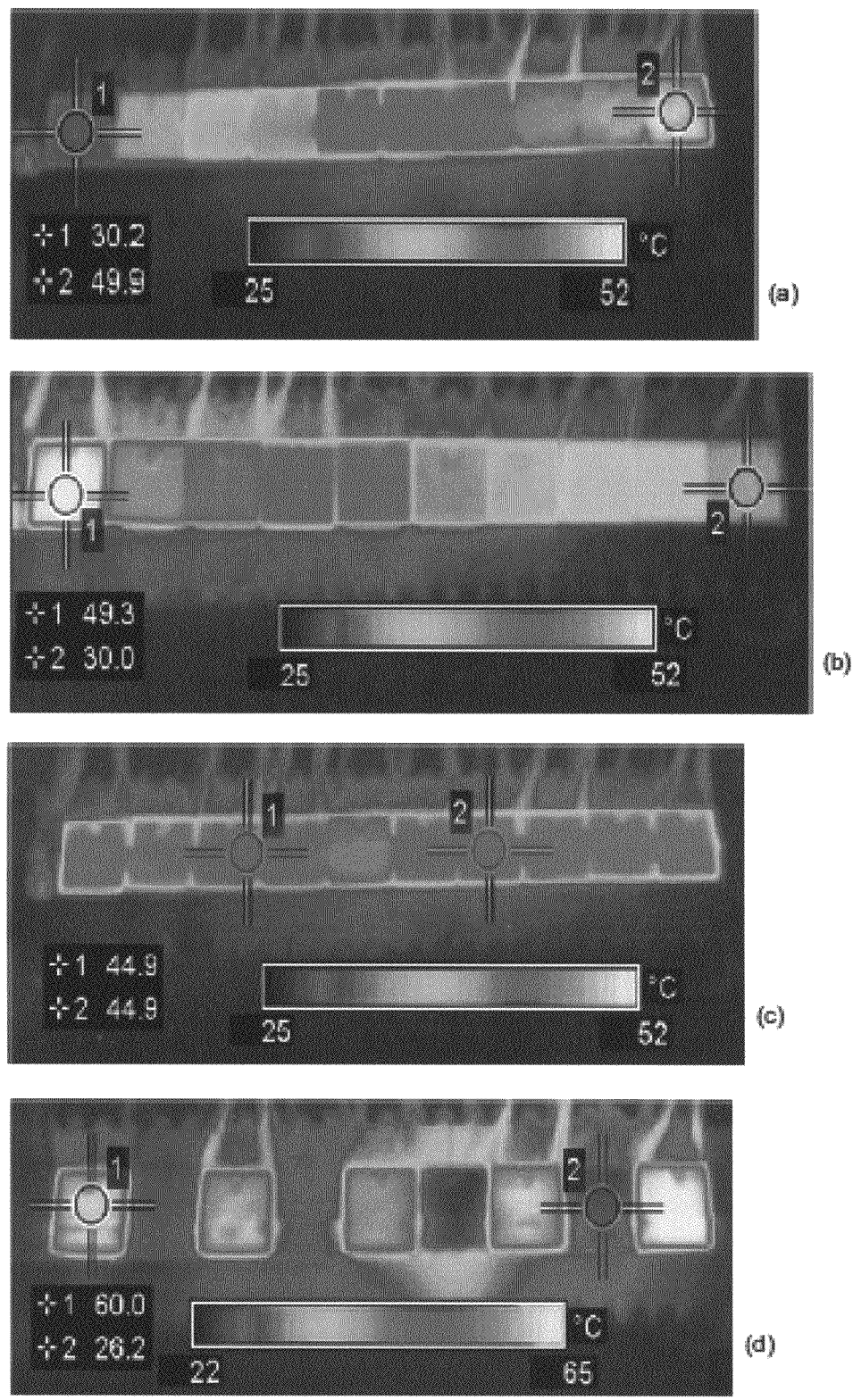
FIG. 6 shows infrared images of TEC column heater with various temperature programs; (a) thermal gradient from 50° C. to 30° C., (b) thermal gradient from 30° C. to 50° C., (c) isothermal operation at 45° C., (d) segmented heating and cooling.

The thermal response of the assembled system was also recorded using a thermal imaging camera. This approach allows the detection of any temperature variations between each of the heating zones and the attached capillary, whilst also allowing real-time monitoring of the thermal equilibration of the column. Any variation in color would indicate that thermal transfer between the TEC units and the column was inefficient and that the column temperature was lower than the units. FIG. 6 shows a series of thermal images of the module, each with a capillary column attached. FIGS. 6(a) and 6(b) show two thermal gradients along the length of the column, from 50° C. to 30° C. and from 30° C. to 50° C. FIG. 6(c) shows the column heater operating in isothermal mode at 45° C. FIG. 6(d) shows how hot and cold zones can be programmed to operate side by side. The latter image shows that there was no heat transfer between zones, which radically distinguishes the TEC based column heater from traditional contact column ovens. Most importantly FIG. 6 shows that the heat generated by each TEC module is transferred directly to the column itself, as the column in each image, and on each individual unit, is not distinguishable from each TEC.

Applications

Chromatographic Application

Figure 7:
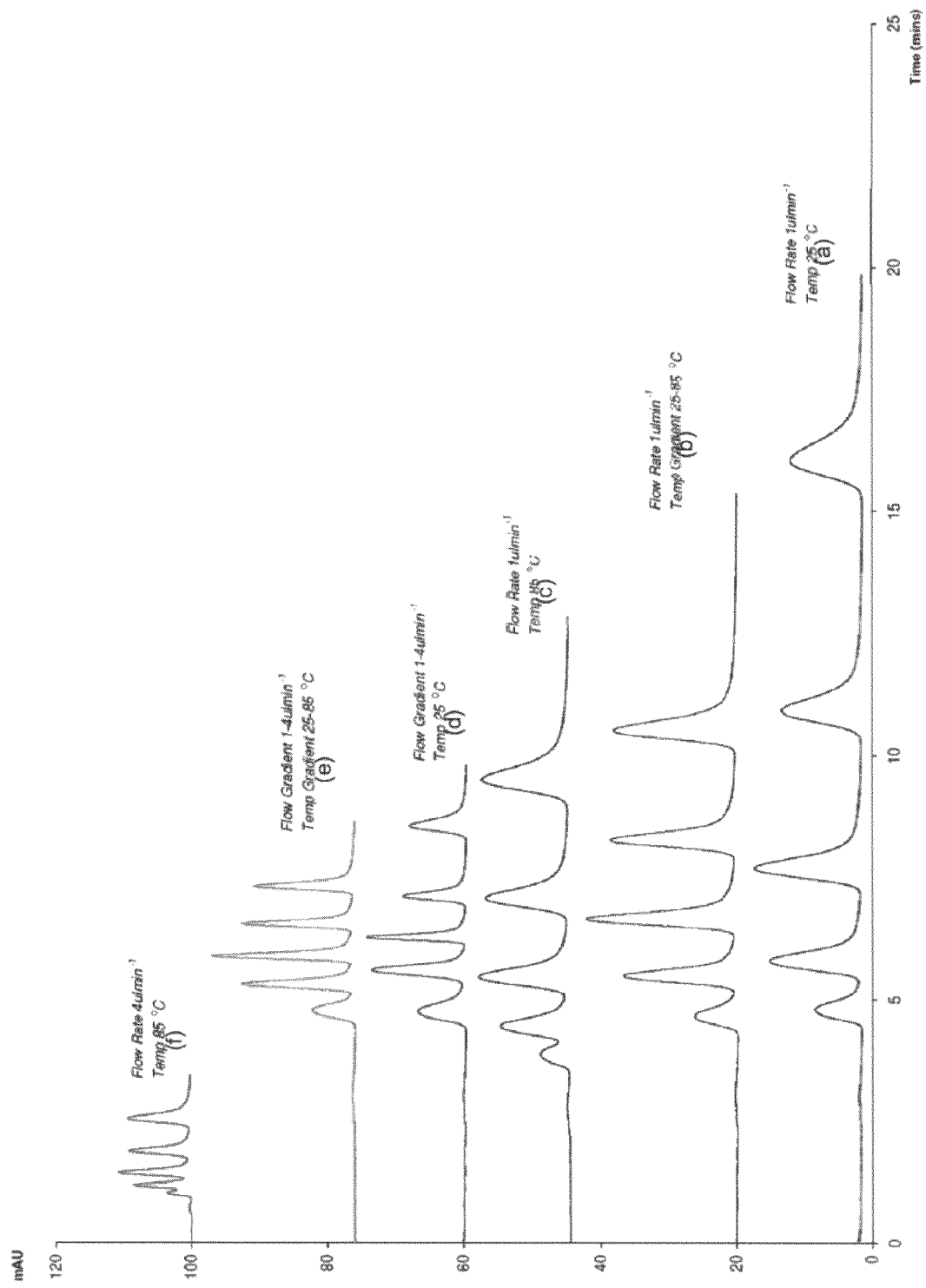
FIG. 7 shows how Separation of 5 alkyl benzenes (toluene, ethyl benzene, propyl benzene, butyl benzene and pentyl benzene) at varying flow rate and temperature; (a) temperature 25° C., flow rate 1 µL min$^{-1}$, (b) temperature gradient 25-85° C. from 3.5 min to 6.5 min, flow rate 1 µL min$^{-1}$, (c) temperature 85° C., flow rate 1 µL min$^{-1}$, (d) temperature 25° C., flow gradient 1-4 µL min$^{-1}$ from 5.3 min to 6.3 min, (e) temperature gradient 25-85° C. from 3.5 min to 6.5 min, flow gradient 1-4 µL min$^{-1}$ from 4.3 min to 8.0 min, (f) temperature 85° C., flow rate 4 µL min$^{-1}$; LMA-EDMA monolithic column, 150 mm×100 µm I.D.; mobile phase 50:50 ACN/$H_2O$. Injection volume=100 nL. UV detection at 254 nm may be achieved in accordance with the present teaching

In order to demonstrate the practical application of a column heater provided within the context of the present teaching for capillary HPLC, in particular its ability to provide rapid thermal gradients, a simple mixture of alkylbenzenes (toluene, ethylbenzene, propylbenzene, butylbenzene, and pentylbenzene) was separated on a reversed-phase LMA-EDMA monolithic capillary column (150 mm×100 µm I.D.) attached to the TEC unit array. The separation was performed under both isothermal and isofluentic conditions, and with various combinations of single and dual temporal gradients of temperature and flow rate. The performed separations are presented in FIG. 7, which shows the chromatograms obtained, with all other parameters, such as analyte concentration, injection volume and mobile phase composition, kept constant. Using a column heater in accordance with the present teaching provides effective separation, with results showing improved peak shapes Initially, a separation of alkylbenzenes was performed under ambient temperature at a set flow rate of 1 µL min$^{-1}$. As shown in FIG. 7(a), under these conditions a complete resolution of all five analytes was achieved on the monolithic column, although the entire separation took approximately 20 minutes. Using the TEC array module set to a constant 85° C., whilst maintaining the flow rate at 1 µL min$^{-1}$, resulted in a faster overall separation, complete in just 12 minutes (see FIG. 7(c)). However, simply increasing the temperature, also resulted in decreased resolution, leaving toluene and ethylbenzene peaks unresolved. Neither was any significant beneficial increase in peak height or area observed, with peak shape (peak width and asymmetry) for both separations approximately the same. Combining the application of high temperature (85° C.) and increased flow rate (4 µL min$^{-1}$) significantly shortened the analysis time to just 4 minutes.

Therefore, in order to speed up the separation while maintaining peak resolution, a series of gradient conditions were investigated. Single gradients of temperature and flow rate were applied separately, and were then compared to a dual temperature/flow gradient. In the first instance, a single temperature gradient from 25° C. to 85° C. was applied from 3.5 min to 6.5 min while maintaining a constant flow rate of 1 µl min$^{-1}$. The start of the temperature gradient was delayed to ensure complete separation of the first two peaks. During the application of the gradient, the column backpressure change was recorded, confirming that the shape of the programmed gradient was identical and simultaneous to that generated by the TEC array module. Comparing chromatograms obtained using the temperature gradient, shown as FIG. 7(b), to the isothermal separations at 25° C. (FIG. 7(a)) and 85° C. (FIG. 7(c)), a reduction in peak width was observed, causing an increase in peak height, whilst simultaneously maintaining asymmetry values and resolution between peaks. It can also be seen that overall separation time decreased by 40% compared with the separation at ambient temperature (FIG. 7a).

In the second instance, a flow gradient from 1 µL min$^{-1}$ to 4 µL min$^{-1}$ was applied from 5.3 min to 6.3 min, while maintaining a constant temperature of 25° C., shown as FIG. 7(d). In this case the start of the flow gradient was delayed to ensure complete separation of the first two peaks. Comparing the peak shapes and overall chromatogram to those achieved under isofluentic conditions at 25° C. (FIG. 7(a)) and 85° C. (FIG. 7(c)), an improvement was observed in peak resolution (compared with FIG. 7(c)), with peaks for toluene and ethylbenzene being fully resolved, while width and asymmetry values noticeably improved (Table 1). In addition, the application of a flow gradient reduced the time separation by 48% compared to the separation at 25° C. (FIG. 7(a)). However, the application of the flow gradient did result in both peak area and height being simultaneously reduced.

Finally, in order to achieve the complete resolution of all peaks, yet maintaining a fast run time, a rapid dual gradient of both flow and temperature was applied, shown here as FIG. 7(e). In this case, an applied temperature gradient was run from 25° C. to 85° C. over 3.5 min to 6.5 min, whilst a simultaneous flow gradient was applied from 1 µL min$^{-1}$ to 4 µL min$^{-1}$ over 5.3 min to 6.3 min. Comparing this separation with the individual gradient runs, namely the temperature gradient (FIG. 7(b)) and flow rate gradient (FIG. 7(d)), it can be seen that the overall separation time has been further reduced to just under 8 minutes, equaling a 66% reduction compared to the isofluentic separation at 25° C. (FIG. 7a). Furthermore, the applied dual gradient resulted in the complete resolution of all sample components, with both peak width and asymmetry improved compared to each of the previous runs, and peak heights generally unaffected.

Fabrication of a Monolith with a Pore Size Gradient

The above chromatographic experiments utilised in-house fabricated polymer monolithic columns. The reproducible production of such monoliths with ideal pore structure for selected applications remains a challenge for separation scientists. It is well known that in order to obtain fine control of monolith porosity during thermal polymerisation, the precise control of the reaction temperature is crucial. The polymerisation process itself is a complex series of reactions, each effected to some degree by the exact system temperature. The most important of these is the initiation rate, which is highly dependent on temperature, since the half-life of initiators decreases with increases in temperature. As a result, the rate of the formation of free radicals, and subsequently, the speed of the chain growth and formation of globules, and the overall polymerisation rate are each higher at elevated temperatures. As the formation of new polymerisation centres is faster than the growth of globules, the supply of monomers runs low fast and the number of globules is large, but their size stays small, leading to smaller voids between globules. Essentially, higher polymerisation temperatures result in smaller flow-through pore sizes.

Figure 9:
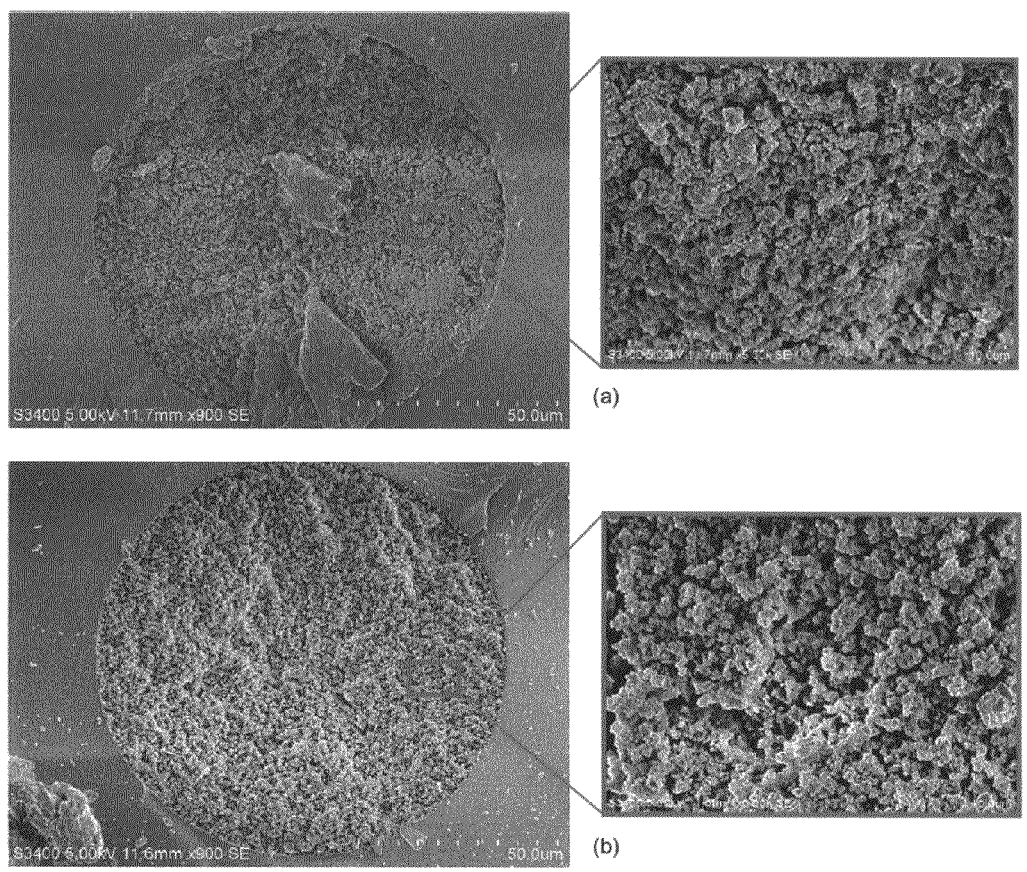
FIG. 9 shows SEM images of BuMA-EDMA monolith formed using a thermal gradient for 16 hours at (a) 60° C. and at (b) 54° C.
Figure 10:
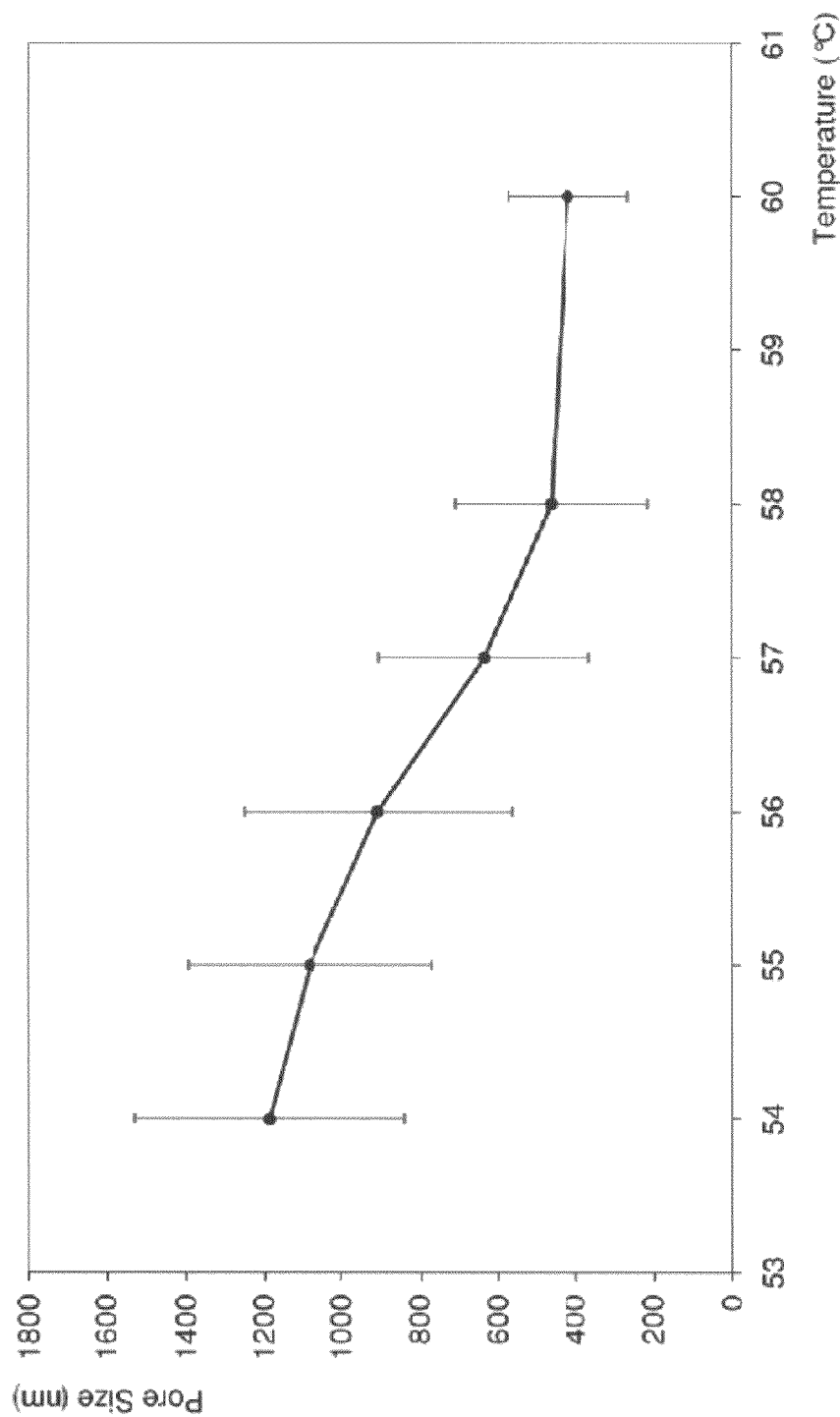
FIG. 10 shows a plot of average pore sizes against increasing polymerisation temperatures for a single capillary housed BuMA-EDMA monolith, polymerised over 16 hours on the TEC array column heater.

The ability of the column heater of the present teaching to precisely control temperature of separate zones within a capillary was exploited to optimise and better understand the fabrication of porous polymer monoliths within capillary columns. In this experiment, the TEC array module was used to polymerise a monolithic column with a longitudinal density gradient. To achieve this, a capillary filled with BuMA-EDMA polymerisation mixture was attached to the TEC units and a heating profile from 60° C. to 54° C. programmed over six distinct thermal zones, with 1° C. spatial increments. Polymerisation of the complete monolith was performed for 16 hours, after which the monolith was washed with MeOH for 1 hour, cut into segments, corresponding to each temperature zone and dried. The porous structure of each of these segments was characterised using SEM. FIG. 9 shows SEM images of two selected zones of the monolith, polymerised at (a) 60° C., and (b) 54° C. It can be clearly seen that the size of polymer globules and flow-through pores differ for these sections. From each of the six sets of segments, the average size (n=30) of the pores were determined and plotted against the exact polymerisation temperature. This relationship is presented as FIG. 10. The graph clearly shows an increase in pore size with a decrease in polymerisation temperature. The graph also shows how the TEC array can also be utilised to produce polymer monoliths of relatively predictable porous structure resulting in the controlled formation of axial gradients of porosity, something very much more difficult to achieve using alternative air heaters, water baths or indeed UV polymerisation approaches.

Application of the TEC Array Module for On-Chip Fabrication of a Polymer Monolithic Stationary Phase With the on-going interest in the development of microfluidic based separations, considerable interest has been focused on the packing and formation of various types of stationary phases in such devices, including monolithic stationary phases. Although there have been various methods established to house such phases into micro-fluidic channels often it is required to polymerise only a specific zone of the channel, and depending on the chip material, UV polymerisation is not always possible. As the column heater of the present teaching can provide both heating and cooling of specific and subsequent zones, its application to the on-chip thermal polymerisation of polystyrene monolithic stationary phases in fixed zones of micro-fluidic channels is apparent. In order to achieve selective polymerisation such as this, the channel was exposed to a well defined thermal profile, which allowed polymerisation to occur in the appropriate heated area, while the area(s) where polymerisation was not desired were simultaneously cooled. Since the individual TEC unit dimensions were 12×12 mm, the polymerised zone in the channel was 12 mm long.

Figure 8:
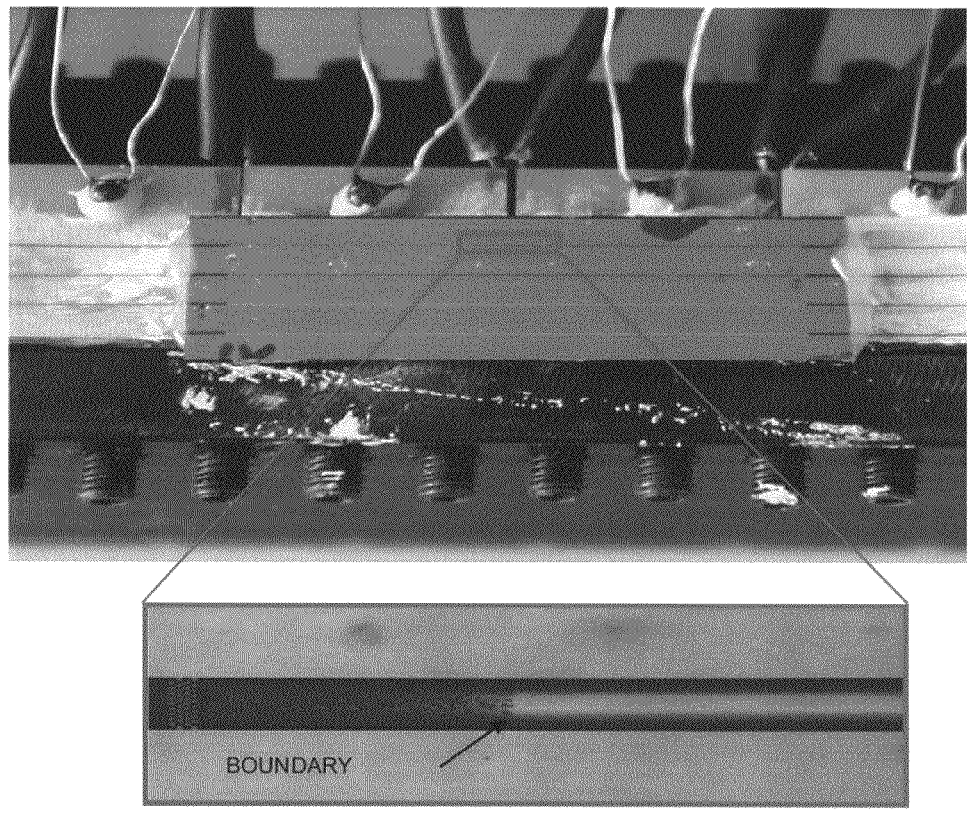
FIG. 8 shows on-chip selective polymerisation of a polystyrene monolith showing the boundary, measured at approximately 100 µm.

For this experiment, a single pre-treated channel (see Experimental Section) of a glass/silica chip (26 mm long with channel dimensions of 50×100 µm) was filled with the styrene monomer mixture. The chip was then attached to the TEC column heater by applying a thin layer of thermally conductive silicon paste between the contact surfaces to ensure a good thermal transfer between the chip and the heater. Due to the large thermal mass of the glass chip, a temperature program was applied to facilitate uniform radial porosity. Specifically, the temperature of the heating zone on the TEC array module was slowly ramped up to the initial dwell temperature of 50° C. over a period of 30 min. This temperature was held for a further 30 min, after which the set point was again increased to the final polymerisation temperature of 60° C. at a rate of 2° C. every 10 min. On either side of the heating zone two cold areas were programmed with a temperature setpoint of 25° C. to prevent thermal polymerisation outside the selected zone. Polymerisation was performed for a period of 24 hrs after which the fabricated monolithic stationary phase in the channel was washed with MeOH. The formed monolith was then inspected under an optical microscope and the boundary between the polymerised and unpolymerised zones was found to be approximately 100 µm (see FIG. 8). This application further demonstrates how the TEC array module is capable of generating very well defined thermal profiles, even when attached to objects with a relatively large thermal mass and high thermal conductivity, such as the glass/silica chip.

CONCLUSIONS

The results presented herein have demonstrated the design and versatile capabilities of a column heater provided in accordance with the present teaching. Such a column heater comprises a plurality of individual heating devices that may be arranged in an array relative to a column that requires heating or cooling. By providing a plurality of such heating devices it is possible to specifically target regions of the column and directly heat or cool those regions as required. While the exemplary column heater described incorporated manual activation of the individual devices it is possible to provide the heater as a self-contained and stand-alone system for example one employing on-board PIC control) with no additional external I/O or acquisition methods required.

A further modification may comprise an I/O link to PC/laptop added for system configuration. To allow further application an eluent pre-heater and fitting heater may be added.

The advantageous use of a direct contact TEC array based column heater/cooler allows for the same heating devices to provide a cooling effect. In accordance with the present teaching it is possible to provide very rapid heating/cooling, exemplary data showing a rate of up to 400° C./min, and that thermal equilibration of the column happens at the same rate.

The application of the heater column to chromatographic separations involving the application of dual temperature/flow rate gradients, with beneficial results has been described. Due to the specific features of thermoelectric modules (precise temperature control, fast response) further demonstrative applications were possible, such as the fabrication of monoliths incorporating a gradient of porosity (in capillary format) and the precise positioning of monoliths with well-defined boundaries in chip formats where in both instances the precise spatial control of temperature during polymerisation is essential.

The advantages of column heater provided in accordance with the present teaching are numerous and include not only advantages of applied temperature, such as increased separation efficiency, variation of peak selectivity, and decreased run times, but also allow spatially application of heated or cooled zones for on-column thermally controlled trap-and-release applications, or to apply instant or dynamic temperature gradients to the column, the latter of provides insights into frictional heating related band broadening processes within capillary columns. Finally, such a heater is useful as a tool in various hyphenated techniques that demand minimal extra column band broadening and require either high and low temperatures, which are outside the normal operating envelope of most column heaters.

It will be appreciated therefore that while exemplary methodologies and devices have been described heretofore that these are provided simply to assist in an understanding of the teaching and benefits of the present invention. Modifications can be made without departing from the spirit and the scope of the present teaching. Integers and steps that are described with reference to one Figure may be interchanged or replaced with those of another Figure without departing from the present teaching.

The words comprises/comprising when used in this specification are to specify the presence of stated features, integers, steps or components but does not preclude the presence or addition of one or more other features, integers, steps, components or groups thereof.

The invention claimed is:

1. A column heater comprising:
a channel for receipt of a column;
a plurality of individual heating devices,
wherein the plurality of heating devices are arranged in an array proximal to, and along a longitudinal axis of, the channel.

2. The heater of claim 1 wherein individual ones of the heating devices operably provide a localized temperature variance proximal to said individual heating device.

3. The heater of claim 1 wherein one or more of the individual heating devices are independently controllable.

4. The heater of claim 1 wherein one or more of the individual ones of the heating devices operably provide a heating effect.

5. The heater of claim 1 wherein one or more of the individual ones of the heating devices operably provide a cooling effect.

6. The heater of claim 2 wherein the array is arranged relative to the channel such that operably the localized temperature variance is induced in a direction transverse to the longitudinal axis of the channel.

7. The heater of claim 1 further comprising a feedback controller and at least one temperature sensor coupled to the feedback controller, the feedback controller configured to provide a control signal to control the operation of one or more of the individual heating devices.

8. The heater of claim 7 wherein the feedback controller comprises a first feedback loop for controlling a heating of the one or more of the individual heating devices and a second feedback loop for controlling a cooling of the one or more of the individual heating devices.

9. The heater of claim 7 wherein the at least one temperature sensor includes a plurality of temperature sensors, individual ones of the temperature sensors being coupled to respective individual ones of the heating devices.

10. The heater of claim 1 wherein the individual heating devices are provided in modular construct allowing the length of the array to be varied dependent on a length of the column that requires heating.

11. The heater of claim 1 wherein the heating devices comprise Peltier thermoelectric (TEC) units.

12. The heater of claim 11 wherein the TEC units are configured to operably provide distinct thermally isolated zones within the channel.

13. The heater of claim 11 wherein the individual Peltier TEC units are provided in a stack arrangement.

14. The heater of claim 13 wherein the stack arrangement is configured to allow a flow of heat in opposing directions.

15. The heater of claim 14 wherein the stack arrangement is configured to operate in a temperature range of less than −10° C. to about 250° C.

16. The heater of claim 1 configured to provide temporal and spatial temperature gradients in a column located within the channel.

17. The heater of claim 1 wherein the individual heating devices are configured to provide a direct contact heating of a column located within the channel.

18. The heater of claim 1 wherein the channel comprises an elastomeric gel within which a column may be seated.

19. The heater of claim 18 wherein the elastomeric gel comprises silicone.

20. The heater of claim 1 wherein the channel is dimensioned to receive a capillary or microscale column.

21. The heater of claim 20 wherein the capillary column is formed from silica.

22. The heater of claim 1 configured to operably spatially apply heated or cooled zones for on-column thermally controlled trap-and-release applications.

23. The heater of claim 1 configured to operably spatially apply heated or cooled zones for on-column thermally responsive polymers.

24. The heater of claim 1 configured to operably apply a dynamic temperature gradient to a column located within the channel.

25. The heater of claim 1 further comprising a heat sink.

26. The heater of claim 1 further comprising a controller configured to provide control signals to individual ones of the one or more heating devices to allow for generation of one or more temporal or spatial temperature gradients in a column located within the channel.

27. The heater of claim 1 wherein the individual heating devices are configured to provide heating and cooling rates of at least 350° C. min$^{-1}$.

28. The heater of claim 1 comprising an eluent pre-heater.

29. The heater of claim 1 wherein at least one of the individual heating devices can be configured to provide post-cooling of a column.

30. The heater of claim 1 wherein at least one of the individual heating devices is configured to provide a heating of fittings of the heater.

31. The heater of claim 1 wherein:
individual ones of the one or more heating devices are formed from Peltier thermoelectric (TEC) units, each of the TEC units provided in a stack arrangement;
the heater further comprising a capillary located within the channel and wherein the capillary is located relative to the TEC units, such that operation of an individual TEC unit provide a direct and localized effect on the capillary bounded by the individual TEC unit.

32. The heater of claim 31 further comprising a resistive heating element.

33. The heater of claim 32 wherein the resistive heating element is interlaced with a stack arrangement of at least one of the TEC units.

34. A capillary heating system comprising:
a channel for receipt of a column;
a plurality of individual active thermal transfer devices, arranged in an array proximal to, and along a longitudinal axis of, the channel;
a capillary located within the channel of the column heater;
a controller configured to independently control operation of the one or more of the active thermal transfer devices to allow generation of one or more temporal or spatial temperature gradients in the capillary.

35. A direct contact segmented column heater comprising a plurality of individual heating devices, each of the individual heating devices being independently controllable, controlled actuation of individual ones of the heating devices operably provided providing a thermal gradient profile within the heater.

* * * * *